United States Patent
Chandrashekhar et al.

(10) Patent No.: US 10,610,532 B2
(45) Date of Patent: Apr. 7, 2020

(54) LIQUID FORMULATIONS OF FOSAPREPITANT

(71) Applicant: LEIUTIS PHARMACEUTICALS PVT. LTD., Hyderabad (IN)

(72) Inventors: Kocherlakota Chandrashekhar, Secunderabad (IN); Banda Nagaraju, Hyderabad (IN)

(73) Assignee: LEIUTIS PHARMACEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 15/750,068

(22) PCT Filed: Aug. 2, 2016

(86) PCT No.: PCT/IB2016/054640
§ 371 (c)(1),
(2) Date: Feb. 2, 2018

(87) PCT Pub. No.: WO2017/021880
PCT Pub. Date: Feb. 9, 2017

(65) Prior Publication Data
US 2018/0235973 A1      Aug. 23, 2018

(30) Foreign Application Priority Data
Aug. 3, 2015   (IN) ............... 4015/CHE/2015

(51) Int. Cl.
| | | |
|---|---|---|
| *A61K 31/5377* | (2006.01) |
| *A61K 9/00* | (2006.01) |
| *A61K 47/40* | (2006.01) |
| *A61P 1/08* | (2006.01) |
| *A61K 47/10* | (2017.01) |
| *A61K 47/18* | (2017.01) |
| *A61K 47/26* | (2006.01) |
| *A61K 47/44* | (2017.01) |

(52) U.S. Cl.
CPC ........ *A61K 31/5377* (2013.01); *A61K 9/0019* (2013.01); *A61K 47/10* (2013.01); *A61K 47/183* (2013.01); *A61K 47/26* (2013.01); *A61K 47/40* (2013.01); *A61K 47/44* (2013.01); *A61P 1/08* (2018.01)

(58) Field of Classification Search
CPC .................................................. A61K 31/5377
See application file for complete search history.

(56) References Cited

U.S. PATENT DOCUMENTS

| | | |
|---|---|---|
| 5,538,982 A | 7/1996 | Hagan et al. |
| 5,691,336 A | 11/1997 | Dorn et al. |
| 5,716,942 A | 11/1998 | Dorn et al. |
| 2007/0265329 A1 | 11/2007 | Devang et al. |

FOREIGN PATENT DOCUMENTS

| | | | |
|---|---|---|---|
| CN | 104414983 A | * 3/2015 | |
| CN | 104414983 A | 3/2015 | |
| WO | 2010018595 A2 | 11/2010 | |
| WO | 2014005606 A1 | 1/2014 | |
| WO | WO-2014005606 A1 | * 1/2014 | ......... A61K 31/5377 |

OTHER PUBLICATIONS

International Search Report and Written Opinion for PCT/IB2016/054640, dated Dec. 15, 2016.
Revision of Emend for Injection Prescribing Information. Aug. 2014.

\* cited by examiner

*Primary Examiner* — Svetlana M Ivanova
(74) *Attorney, Agent, or Firm* — Heslin Rothenberg Farley & Mesiti P.C.

(57) ABSTRACT

The present invention relates to liquid formulations of Fosaprepitant intended for parenteral administration. Further the invention also describes process for preparing such formulations.

17 Claims, No Drawings

LIQUID FORMULATIONS OF FOSAPREPITANT

CROSS REFERENCE TO RELATED APPLICATIONS

This application is a U.S. National Phase filing under 35 U.S.C. § 371 of International Application PCT/IB2016/054640, filed Aug. 2, 2016, and published as WO 2017/021880 A1 on Feb. 9, 2017. PCT/IB2016/054640 claims priority from Indian application number 4015/CHE/2015, filed Aug. 3, 2015. The entire contents of each of these applications are hereby incorporated herein by reference.

BACKGROUND OF THE INVENTION

Fosaprepitant is a P/neurokinin-1 (NK1) receptor antagonist and is a prodrug of Aprepitant. The meglumine salt of Fosaprepitant, Fosaprepitant dimeglumine, is approved in the U.S as Emend® in the form of a lyophilized powder for intravenous infusion. Fosaprepitant dimeglumine is rapidly converted to Aprepitant in vivo. It is chemically described as 1-deoxy-1-(methylamino)-D-glucitol[3-[[(2R,3S)-2-[(1R)-1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]phosphonate (2:1) having an empirical formula $C_{23}H_{22}F_7N_4O_6P.2(C_7H_{17}NO_5)$. The structure is depicted below:

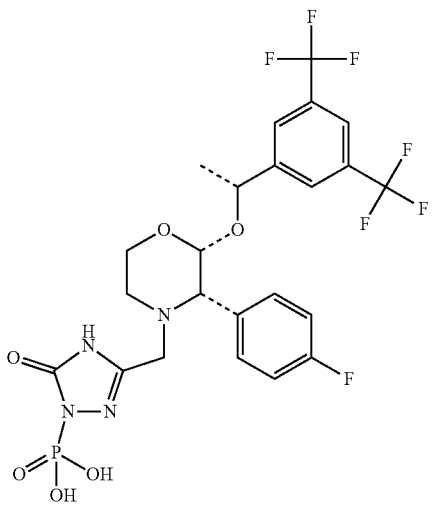 [SMILES: C[C@@H](O[C@H]1OCCN(Cc2nn(P(=O)(O)O)c(=O)[nH]2)[C@H]1c1ccc(F)cc1)c1cc(C(F)(F)F)cc(C(F)(F)F)c1]

Emend® is indicated in adults for use in combination with other antiemetic agents for the prevention of acute and delayed nausea and vomiting associated with initial and repeat courses of highly emetogenic cancer chemotherapy including high-dose cisplatin.

U.S. Pat. No. 5,691,336 to Dorn et al, discloses the compound Fosaprepitant and further describes methods of synthesizing the said compound. U.S. Pat. No. 5,716,942 also to Dorn et al., discloses the use of neurokinin 1 receptor antagonist such as Fosaprepitant for the treatment of inflammatory diseases, pain or migraine, asthma, emesis and nausea.

U.S patent application No. 2007/265329 to Devang et al., discloses subcutaneous pharmaceutical injectable composition comprising a semi-solid delivery vehicle and a pharmaceutically acceptable liquid vehicle, for the sustained release of a 5-HT3 receptor antagonist in the treatment of chemotherapy-induced nausea and vomiting.

U.S. Pat. No. 5,538,982 to Hagan et al., discloses a NK, receptor antagonist for the treatment of emesis and further discloses neurokinin 1 receptor antagonist in combination with anti-inflammatory corticosteroid or a 5HT3 antagonist.

Fosaprepitant dimeglumine easily degrades to Aprepitant unless stored at low temperature. Therefore it is conventionally supplied as a lyophilized formulation to reduce the formation of impurities and to improve the stability of the final formulation.

This invention is directed to stable liquid parenteral formulations of Fosaprepitant that do not need reconstitution before administration.

SUMMARY OF THE INVENTION

The present invention relates to stable, liquid parenteral pharmaceutical formulation of Fosaprepitant and method of preparing such compositions.

One aspect of the invention provides stable liquid parenteral pharmaceutical formulation of Fosaprepitant, wherein the pH of the formulation ranges from about 7 to 13.

Another aspect of the present invention relates to liquid parenteral pharmaceutical formulation of Fosaprepitant comprising of Fosaprepitant, chelating agents, pH adjusting agents/buffering agents, stabilizing agents, solvents and optionally other pharmaceutically acceptable adjuvants.

Another aspect of the invention provides method for preparing liquid parenteral pharmaceutical formulation comprising of Fosaprepitant dimeglumine, chelating agents, pH adjusting agents/buffering agents, stabilizing agents, solvents and optionally other pharmaceutically acceptable adjuvants.

DETAILED DESCRIPTION OF THE INVENTION

In the context of this invention "Fosaprepitant" refers to pharmaceutically acceptable salts, solvates, hydrates, acids and anhydrous forms thereof, preferably Fosaprepitant dimeglumine.

As used herein, "liquid parenteral pharmaceutical formulations of Fosaprepitant" refer to formulations that contain Fosaprepitant in dissolved or solubilized form and are intended to be used as such or upon further dilution in intravenous diluents.

The term "about" is meant to encompass a pH range of ±0.5 from the specified value or range.

The present invention relates to liquid parenteral formulations of Fosaprepitant which are stable upon storage. Developing liquid formulations of Fosaprepitant has proven to be difficult due to its rapid conversion to Aprepitant which is not water soluble.

The inventors of the present invention have surprisingly found that it is possible to develop stable liquid parenteral pharmaceutical formulation of Fosaprepitant, despite rapid degradation of Fosaprepitant to Aprepitant.

An embodiment of the invention provides liquid parenteral pharmaceutical formulation of Fosaprepitant having a pH in the range of about 7 to 13. More specifically, the invention provides liquid parenteral pharmaceutical formulation of Fosaprepitant having a pH in the range of 6.5 to 13.5.

Another embodiment of the invention provides liquid parenteral pharmaceutical formulation of Fosaprepitant comprising:
   i. Fosaprepitant
   ii. chelating agents
   iii. stabilizing agents
   iv. pH adjusting agents and/or buffering agents
   v. solvents and
   vi. optionally other pharmaceutically acceptable adjuvants.

Yet another embodiment of the invention provides liquid parenteral pharmaceutical formulation of Fosaprepitant comprising:
   i. Fosaprepitant dimeglumine
   ii. chelating agents selected from EDTA, DTPA, DOTA and salts thereof
   iii. one or more stabilizing agents selected from surfactants and cyclodextrins
   iv. pH adjusting agents and/or buffering agents
   v. solvents selected from the group comprising of propylene glycol, glycerine polyethylene glycol and water
   vi. optionally other pharmaceutically acceptable adjuvants.

The pharmaceutical compositions of the present invention contains chelating agents selected from the group comprising, EDTA (Ethylene diamine tetra acetic acid), DOTA (1,4,7,10-tetraazacyclododecane-1,4,7,10-tetraacetic acid), DTPA (diethylenetriamine pentaacetic acid), EGTA (ethylene glycol-bis(β-aminoethyl ether)-N,N,N',N'-tetraacetic acid), HEDTA (N (hydroxy ethyl) ethylenediaminetriacetic acid) and salts thereof. Preferred chelating agent is disodium edetate. The percentage of chelating agent ranges from about 0.01% to 5% based on total weight of the formulation.

Suitable stabilizing agents include surfactants such as polysorbates, polyethylene glycol esters, sorbitan esters (e.g. Tweens), polyoxyethylated vegetable oil, polyethoxylated castor oil, sucrose fatty acid esters and cyclodextrins such as α, β and γ-cyclodextrin and cyclodextrins modified with alkyl-, hydroxyalkyl-, dialkyl-, and sulfoalkyl-ether modified cyclodextrins such as methyl or hydroxypropyl β-cyclodextrins (HPCD), methyl-and-ethyl-β-cyclodextrin, sulfoalkylether-substituted beta-cyclodextrin, sulfobutylether-β-cyclodextrin (SBECD) and salts thereof. Preferred stabilizing agents are polysorbates and cyclodextrins. The percentage of stabilizing agent ranges from about 0.05% to 30% based on total weight of the formulation.

Suitable pH adjusting agents and buffering agents that may be used in the invention include phosphate buffer, citrate buffer, sodium carbonate, sodium bicarbonate, tartarate, benzoate, acetate, borate, lactic acid, glutaric acid, malic acid, succinic acid and carbonic acid, alkali or alkaline earth salt of one of these acids, Tris, meglumine, amino acids such as arginine, glycine, histidine and lysine; sodium hydroxide, potassium hydroxide, ammonium carbonate, hydrochloric acid, citric acid, phosphoric acid and the like.

Suitable solvents include ethanol, glycerine, propylene glycol, polyethylene glycol, water and the like. Water is the preferred solvent. Percentage of the solvent ranges from about 30% to 98%, based on total weight of the formulation.

The pharmaceutical compositions of the present invention may also contain anti-oxidants and tonicity modifiers.

The inventors carried out experiments with varying the pH value of formulation to determine suitable pH range in the final formulation. Fosaprepitant formulations prepared were tested at 25±2° C. temperature.

TABLE 1

Evaluation of pH on stability of the formulation (Prepared according to example 6)

| pH | Hold time | Assay | Related substances (%) | |
|---|---|---|---|---|
| | | | Aprepitant | Total impurities |
| 7.5 | 6 hrs | 99.5 | 0.31 | 0.45 |
| | 12 hrs | 99.5 | 0.33 | 0.49 |
| 8.5 | 6 hrs | 99.6 | 0.25 | 0.39 |
| | 12 hrs | 99.6 | 0.25 | 0.41 |
| 9.2 | 6 hrs | 99.6 | 0.23 | 0.41 |
| | 12 hrs | 99.6 | 0.23 | 0.41 |
| 10.5 | 6 hrs | 99.6 | 0.28 | 0.43 |
| | 12 hrs | 99.6 | 0.28 | 0.45 |
| 11.5 | 6 hrs | 99.6 | 0.27 | 0.44 |
| | 12 hrs | 99.6 | 0.27 | 0.44 |

In one of the preferred embodiment, liquid parenteral pharmaceutical formulations of Fosaprepitant comprise:

| | |
|---|---|
| i) Fosaprepitant dimeglumine | 0.1%-15% |
| ii) chelating agent | 0.01%-5% |
| iii) stabilizing agents | 0.05%-30% |
| iv) solvent | 30%-98% |
| v) pH adjusting agents and/or buffering agents | q.s |
| based on total weight of the formulation. | |

The compositions of the present invention can be prepared using the following manufacturing steps:
   i. Addition of pH adjusting agents and/or buffering agents to the solvent.
   ii. Addition of stabilizing agent to the solution followed by stirring till uniform solution is obtained, maintaining the temperature at about 25° C.
   iii. Cooling of the above bulk solution to 2° C. to 8° C.
   iv. Addition of Fosaprepitant to the solution obtained, followed by stirring and pH adjustment, while maintaining the temperature at 2° C. to 8° C.
   v. Filtering and filling of the solution in suitable container or vials followed by stoppering and sealing of the vials.

Fosaprepitant formulation prepared according to the invention was tested for stability at 2-8° C. and 25° C./60% RH for a period of 3 months. The stability data of the invention formulation is summarized in table 2.

TABLE 2

Stability data of the product prepared according to example 10. Fosaprepitant dimeglumine injection stability profile

| | 1 M | | 2 M | | 3 M | |
|---|---|---|---|---|---|---|
| Condition | 2-8° C. | 25° C. | 2-8° C. | 25° C. | 2-8° C. | 25° C. |
| | | | Impurities | | | |
| Aprepitant | 0.32 | 0.66 | 0.34 | 1.23 | 0.3 | 1.26 |
| Total Impurities | 0.61 | 0.95 | 0.60 | 1.48 | 0.56 | 1.59 |
| Assay | 100.5 | 98.0 | 100.4 | 99.0 | 101.7 | 97.6 |

Surprisingly no significant increase in impurities was observed even at accelerated conditions. The data confirms the inventors' finding that Fosaprepitant formulations in the presence of suitable excipients resulted in a stable product.

The following examples further describe certain specific aspects and embodiments of the present invention and demonstrate the practice and advantages thereof. It is to be understood that the examples are given by way of illustration only and are not intended to limit the scope of the invention in any manner.

Example 1

| Ingredients | Qty/ml (mg) |
|---|---|
| Fosaprepitant dimeglumine | 49.06 |
| Disodium edetate | 2-8 |
| Polysorbate 80 | 5-40 |
| Sodium carbonate | 0.5-10 |
| Sodium bicarbonate | 5-30 |
| Sodium chloride | q.s |
| Sodium hydroxide | q.s to adjust the pH 11.0 ± 1.0 |
| Water for injection | q.s to 1 ml |

*q.s: Quantity sufficient

Manufacturing Process

Water for injection was taken in a compounding vessel and disodium edetate was added and stirred. Sodium carbonate was added, followed by the addition of sodium bicarbonate. Sodium chloride and polysorbate 80 were added to the above solution. The bulk solution was cooled to 2-8° C. Fosaprepitant dimeglumine was added, and the pH of the solution was adjusted with sodium hydroxide, while maintaining the temperature at 2-8° C. The solution was filtered, followed by stoppering and sealing of the vials.

Example 2

| | Quantities in mg | | |
|---|---|---|---|
| Ingredients | F-I | F-II | F-III |
| Fosaprepitant dimeglumine | 49.06 | 49.06 | 49.06 |
| Disodium edetate | 2-8 | 2-8 | 2-8 |
| Polysorbate-80 | 5-40 | 5-40 | 5-40 |
| Sodium carbonate | 0.5-10 | 0.5-10 | — |
| Sodium bicarbonate | 5-30 | 5-30 | — |
| Arginine | — | — | 10-20 |
| Mannitol | — | q.s | — |
| Sodium chloride | q.s | — | q.s |
| Sodium hydroxide | q.s to adjust the pH 11.0 ± 1.0 | | |
| Water for injection | q.s to 1 ml | | |

Manufacturing Process

Water for injection was taken in a compounding vessel and disodium edetate was added and stirred. Sodium carbonate and sodium bicarbonate/arginine were added. Sodium chloride/mannitol and polysorbate 80 were added to the above solution. The bulk solution was cooled to 2-8° C. Fosaprepitant dimeglumine was added, and the pH of the solution was adjusted with sodium hydroxide, while maintaining the temperature at 2-8° C. The solution was filtered, followed by stoppering and sealing of the vials.

TABLE 3

Stability data of the product prepared according to example 2.

| | Quantities in mg | | |
|---|---|---|---|
| pH adjusting agents | F-I | F-II | F-III |
| Sodium carbonate | 1.2 | 1.2 | — |
| Sodium bicarbonate | 10 | 10 | — |
| Arginine | — | — | 17.42 |

| | 1 Mo | 3 Mo | 6 Mo | 1 Mo | 3 Mo | 6 Mo | 1 Mo | 3 Mo | 6 Mo |
|---|---|---|---|---|---|---|---|---|---|
| Observations | | | | | | | | | |
| 2-8° C. | | | | | | | | | |
| pH of the solution | 10.9 | 11.3 | 10.9 | 10.9 | 11.31 | 10.9 | 10.9 | 11.4 | 10.9 |
| Assay (%) | 102.0 | 100 | 100 | 102 | 102 | 99.0 | 102.3 | 101.8 | 99.2 |
| Related substances | | | | | | | | | |
| Aprepitant | 0.14 | 0.27 | 0.34 | 0.14 | 0.26 | 0.33 | 0.15 | 0.28 | 0.37 |
| Total impurities | 0.47 | 0.71 | 0.92 | 0.47 | 0.73 | 0.93 | 0.45 | 0.77 | 1.07 |
| 25 ± 2° C./ 60 ± 5% RH | | | | | | | | | |
| pH of the solution | 10.9 | 11.2 | 10.8 | 10.9 | 11.2 | 10.8 | 10.8 | 11.3 | 10.8 |
| Assay (%) | 101.6 | 97.9 | 95.9 | 101.9 | 101.8 | 96.3 | 98.6 | 98.4 | 94.30 |
| Related substances | | | | | | | | | |
| Aprepitant | 0.62 | 1.33 | 2.58 | 0.61 | 1.31 | 2.40 | 0.83 | 1.85 | 3.67 |
| Total impurities | 0.92 | 1.94 | 3.53 | 0.92 | 1.94 | 3.38 | 1.13 | 2.51 | 4.59 |

Example 3

| Ingredients | Qty/ml (mg) |
| --- | --- |
| Fosaprepitant dimeglumine | 49.06 |
| Disodium edetate | 2-8 |
| Polysorbate 80 | 5-40 |
| Sodium carbonate | 0.5-10 |
| Sodium bicarbonate | 5-30 |
| Mannitol | q.s |
| Sodium hydroxide | q.s to adjust the pH 11.0 ± 1.0 |
| Water for injection | q.s to 1.0 mL |

Manufacturing Process

Water for injection was taken in a compounding vessel and disodium edetate was added and stirred. Sodium carbonate was added, followed by the addition of sodium bicarbonate. Mannitol and polysorbate 80 were added to the above solution. The bulk solution was cooled to 2-8° C. Fosaprepitant dimeglumine was added, and the pH of the solution was adjusted with sodium hydroxide, while maintaining the temperature at 2-8° C. The solution was filtered, followed by stoppering and sealing of the vials.

Example 4

| Ingredients | Qty/ml (mg) |
| --- | --- |
| Fosaprepitant dimeglumine | 49.06 |
| Disodium edetate | 2-8 |
| Polysorbate-80 | 5-40 |
| Glycine | 5-25 |
| Lactose | q.s |
| Sodium hydroxide | q.s to adjust the pH 11.0 ± 1.0 |
| Water for injection | q.s to 0.5 ml to 2.0 mL |

Manufacturing Process

Water for injection was taken in a compounding vessel and disodium edetate was added and stirred. Glycine was added. Lactose and polysorbate 80 were added to the above solution. The bulk solution was cooled to 2-8° C. Fosaprepitant dimeglumine was added, and the pH of the solution was adjusted with sodium hydroxide, while maintaining the temperature at 2-8° C. The solution was filtered, followed by stoppering and sealing of the vials.

Example 5

| Ingredients | Qty/ml (mg) |
| --- | --- |
| Fosaprepitant dimeglumine | 49.06 |
| Disodium edetate | 2-8 |
| Polysorbate-80 | 5-40 |
| TRIS | 2-20 |
| Sucrose | q.s |
| Sodium hydroxide | q.s to adjust the pH 11.0 ± 1.0 |
| Water for injection | q.s to 0.5 ml to 2.0 mL |

Manufacturing Process

Water for injection was taken in a compounding vessel and disodium edetate was added and stirred. TRIS buffer was added. Sucrose and polysorbate 80 were added to the above solution. The bulk solution was cooled to 2-8° C. Fosaprepitant dimeglumine was added, and the pH of the solution was adjusted with sodium hydroxide, while maintaining the temperature at 2-8° C. The solution was filtered, followed by stoppering and sealing of the vials.

Example 6

| Ingredients | Qty per vial (mg) |
| --- | --- |
| Fosaprepitant dimeglumine | 188.0 mg |
| Lactose monohydrate | 302.62 mg |
| Edetate disodium | 14.4 mg |
| Polysorbate 80 | 57.5 mg |
| Sodium hydroxide | q.s to adjust pH 9.1 to 9.4 |
| Hydrochloric acid | |
| Water for injection | q.s to 2.6 mL |

Manufacturing Process

Water for injection was taken in a compounding vessel and lactose and disodium edetate were added and stirred. The bulk solution was cooled to 2-8° C. Fosaprepitant dimeglumine was added, followed by the addition of polysorbate 80 to the above solution. pH of the solution was adjusted with sodium hydroxide solution/hydrochloric acid while maintaining the temperature at 2-8° C. The solution was filtered, followed by stoppering and sealing of the vials.

Example 7

| Ingredients | Qty per ml (mg) |
| --- | --- |
| Fosaprepitant dimeglumine | 49.06 |
| Edetate disodium | 3.76 |
| Sulfobutyl-ether-β-cyclodextrin sodium salt | 150 |
| Sodium carbonate | 1.2 |
| Sodium bicarbonate | 10 |
| Sodium hydroxide | q.s to adjust pH around 10 |
| Water for injection | q.s to 1 ml |

Manufacturing Process

Water for injection was taken in a compounding vessel. Sodium carbonate and sodium bicarbonate were added and stirred, followed by the addition of edetate disodium. Sulfobutyl-ether-β-cyclodextrin sodium salt was added and stirred till a clear solution was obtained. The bulk solution was cooled to 2-8° C. Fosaprepitant dimeglumine was added to the above solution and pH was adjusted with sodium hydroxide solution while maintaining the temperature at 2-8° C. The solution was filtered, followed by stoppering and sealing of the vials.

Example 8

| Ingredients | Qty per ml (mg) |
| --- | --- |
| Fosaprepitant dimeglumine | 49.06 |
| Edetate disodium | 3.76 |
| Sulfobutyl-ether-β-cyclodextrin sodium salt | 50 |
| Sodium hydroxide | q.s to adjust pH around 10 |
| Water for injection | q.s to 1 ml |

Manufacturing Process

Water for injection was taken in a compounding vessel. Edetate disodium was added and stirred. Sulfobutyl-ether-β-cyclodextrin sodium salt was added and stirred till a clear solution was obtained. The bulk solution was cooled to 2-8° C. Fosaprepitant dimeglumine was added, to the above solution and pH was adjusted with sodium hydroxide solution while maintaining the temperature at 2-8° C. The solution was filtered, followed by stoppering and sealing of the vials.

Example 9

| Ingredients | Qty per ml (mg) |
| --- | --- |
| Fosaprepitant dimeglumine | 49.06 |
| Edetate disodium | 3.76 |
| Sulfobutyl-ether-β-cyclodextrin sodium salt | 30 |
| Polysorbate 80 | 20 |
| Sodium carbonate | 1.2 |
| Sodium bicarbonate | 10 |
| Sodium chloride | 0.6 |
| Sodium hydroxide | q.s to adjust pH around 10 |
| Water for injection | q.s to 1 ml |

Manufacturing Process

Water for injection was taken in a compounding vessel. Sodium carbonate and sodium bicarbonate were added and stirred, followed by the addition of edetate disodium and sodium chloride. Sulfobutyl-ether-β-cyclodextrin sodium salt was added and then polysorbate 80 was added and stirred till a clear solution was obtained. The bulk solution was cooled to 2-8° C. Fosaprepitant dimeglumine was added to the above solution and pH was adjusted with sodium hydroxide solution while maintaining the temperature at 2-8° C. The solution was filtered, followed by stoppering and sealing of the vials.

Example 10

| Ingredients | Quantity per mL |
| --- | --- |
| Fosaprepitant dimeglumine | 4.91 mg |
| Edetate disodium | 0.376 mg |
| Hydroxy propyl beta cyclodextrin | 49.1 mg |
| Sodium carbonate anhydrous | 0.24 mg |
| Sodium bicarbonate | 2.0 mg |
| Sodium chloride | 6.0 mg |
| Sodium hydroxide | 0.80 mg |
| Water for injection | q.s to 1 mL |

Manufacturing Process

Water for injection was taken in a compounding vessel. Sodium hydroxide was added, followed by the addition of hydroxy propyl beta cyclodextrin to the above solution. The solution was cooled to 2-8° C. Fosaprepitant dimeglumine was added and stirred. Edetate disodium was added followed by the addition of sodium carbonate anhydrous and sodium bicarbonate. Finally Sodium chloride was added to the above solution. The solution was filtered, followed by stoppering and sealing of the vials.

Example 11

| Ingredients | Quantity per mL |
| --- | --- |
| Fosaprepitant dimeglumine | 4.91 mg |
| Edetate disodium | 0.376 mg |
| Hydroxy propyl beta cyclodextrin | 196.4 mg |
| Sodium carbonate anhydrous | 0.24 mg |
| Sodium bicarbonate | 2.0 mg |
| Sodium chloride | 6.0 mg |
| Sodium hydroxide/Hydrochloric acid | q.s to adjust the pH to 7.0-7.5 |
| Water for injection | q.s to 1 mL |

Manufacturing Process

Water for injection was taken in a compounding vessel. Sodium hydroxide was added, followed by the addition of hydroxy propyl beta cyclodextrin to the above solution. The solution was cooled to 2-8° C. Fosaprepitant dimeglumine was added and stirred. Edetate disodium was added followed by the addition of sodium carbonate anhydrous and sodium bicarbonate. Finally sodium chloride was added to the above solution. The solution was filtered, followed by stoppering and sealing of the vials.

We claim:

1. A stable, liquid parenteral pharmaceutical formulation of Fosaprepitant comprising:
    (i) Fosaprepitant dimeglumine from approximately 0.1% to 15% w/w based on the total weight of the formulation;
    (ii) one or more chelating agents, at a concentration from approximately 0.01% to approximately 5% w/w based on the total weight of the formulation;
    (iii) one or more stabilizing agents selected from polysorbates and β-cyclodextrins;
    (iv) one or more pH adjusting agents and/or buffering agents;
    (v) one or more solvents;
    (vi) a pH ranging from 7 to 13; and
    (vii) optionally other pharmaceutically acceptable excipients.

2. The stable, liquid parenteral pharmaceutical formulation of claim 1 comprising
    (i) the one or more chelating agents are selected from EDTA, DTPA, DOTA and salts thereof;
    (ii) the one or more solvents are selected from propylene glycol, glycerine, polyethylene glycol and water.

3. The stable, liquid parenteral pharmaceutical formulation of claim 2, wherein the one or more stabilizing agents is polysorbate 80.

4. The stable, liquid parenteral pharmaceutical formulation of claim 2, wherein the β-cyclodextrins are selected from hydroxypropyl β-cyclodextrin (HPβCD) and sulfobutylether-β-cyclodextrin (SBECD).

5. The stable, liquid parenteral pharmaceutical formulation of claim 2, wherein the pH adjusting agents and/or buffering agents are selected from one or more of: phosphate buffer, citrate buffer, sodium carbonate, sodium bicarbonate, tartarate, benzoate, lactate, acetate, borate, glutaric acid, malic acid, succinic acid and carbonic acid, alkali or alkaline earth salt of one of these acids, Tris, histidine, meglumine, amino acids, sodium hydroxide, potassium hydroxide, hydrochloric acid and citric acid.

6. The stable liquid parenteral formulation of claim 1 wherein the chelating agent is EDTA.

7. The stable liquid parenteral formulation of claim 1 wherein the one or more pharmaceutically acceptable excipients is an amino acid selected from the group consisting of arginine, glycine, histidine and lysine.

8. The stable liquid parenteral formulation of claim 1 wherein the one or more pharmaceutically acceptable excipients is arginine.

9. The stable liquid parenteral formulation of claim 1 wherein the one or more pharmaceutically acceptable excipients is one or more tonicity modifiers.

10. The stable liquid parenteral formulation of claim 1 wherein the one or more tonicity modifiers is mannitol.

11. The stable liquid parenteral formulation of claim 1 wherein the one or more stabilizing agents are one or more β-cyclodextrins.

12. The stable liquid parenteral formulation of claim 1, wherein the one or more stabilizing agents is sulfobutyl-ether-β-cyclodextrin sodium salt.

13. The stable liquid parenteral formulation of claim 1, wherein the quantity of the one or more stabilizing agents is from approximately 0.05% w/w to approximately 30% based on total weight of the formulation.

14. The stable liquid parenteral formulation of claim 1, wherein the one or more stabilizing agents is hydroxy propyl beta cyclodextrin.

15. The stable liquid parenteral formulation of claim 1, wherein after storage at 2-8° C. for at least 1 month, the concentration of aprepitant is not more than 10%.

16. The stable liquid parenteral formulation of claim 1, wherein after storage at 2-8° C. for at least 1 month, the concentration of aprepitant is not more than 2%.

17. The stable liquid parenteral formulation of claim 2, wherein the EDTA is present from approximately 0.1% to approximately 1.6% w/w based on the total weight of the formulation.

* * * * *